(12) United States Patent
Gamache et al.

(10) Patent No.: US 8,104,506 B2
(45) Date of Patent: Jan. 31, 2012

(54) DIAPHRAGM-SEALED VALVE HAVING INTERMEDIATE COMMUNICATION PORTS

(75) Inventors: Yves Gamache, Adstock (CA); Andre Fortier, Adstock (CA)

(73) Assignee: Mecanique Analytique Inc., Thetford-Mines (Quebec) (CA)

( * ) Notice: Subject to any disclaimer, the term of this patent is extended or adjusted under 35 U.S.C. 154(b) by 873 days.

(21) Appl. No.: 12/170,853

(22) Filed: Jul. 10, 2008

(65) Prior Publication Data

US 2009/0014078 A1 Jan. 15, 2009

Related U.S. Application Data

(60) Provisional application No. 60/929,704, filed on Jul. 10, 2007.

(51) Int. Cl.
*F16K 7/16* (2006.01)
(52) U.S. Cl. .............................. 137/597; 251/331
(58) Field of Classification Search .................. 137/597; 251/331
See application file for complete search history.

(56) References Cited

U.S. PATENT DOCUMENTS

| | | | |
|---|---|---|---|
| 2,865,402 A * | 12/1958 | Miller | 137/637.1 |
| 2,989,082 A * | 6/1961 | Ray | 137/625.46 |
| 3,085,440 A | 4/1963 | Guenther | |
| 3,111,849 A | 11/1963 | Broerman | |
| 3,139,755 A | 7/1964 | Reinecke et al. | |
| 3,140,615 A | 7/1964 | Broerman | |
| 3,198,018 A | 8/1965 | Broerman | |
| 3,376,894 A | 4/1968 | Broerman | |
| 3,387,496 A | 6/1968 | Broerman | |
| 3,417,605 A | 12/1968 | Hahn | |
| 3,439,542 A | 4/1969 | McCray | |
| 3,492,873 A | 2/1970 | Broerman et al. | |
| 3,545,491 A | 12/1970 | Broerman | |
| 3,633,426 A | 1/1972 | Broerman | |
| 4,068,528 A * | 1/1978 | Gundelfinger | 73/864.84 |
| 4,112,766 A | 9/1978 | Ragains | |
| 4,276,907 A | 7/1981 | Broerman | |
| 4,304,257 A * | 12/1981 | Webster | 137/559 |
| 4,333,500 A | 6/1982 | Broerman | |
| 5,193,581 A * | 3/1993 | Shiroto et al. | 137/625.11 |
| 5,601,115 A | 2/1997 | Broerman | |
| 6,202,698 B1 | 3/2001 | Stearns | |
| 6,742,544 B2 * | 6/2004 | Bergh et al. | 137/885 |
| 2006/0042686 A1 | 3/2006 | Gamache et al. | |

* cited by examiner

*Primary Examiner* — John Fox
(74) *Attorney, Agent, or Firm* — Fish & Richardson P.C.

(57) ABSTRACT

A diaphragm-sealed valve having communication mechanisms operatively connecting neighboring pairs of grooves is provided. Each communication mechanism has a communication port opening in an interface of a valve cap, between the neighboring grooves. The communication mechanism also has a communication conduit extending within the valve cap and connecting the communication port and one of the neighboring grooves. It also has a recess within a valve body aligned with the communication port and with the other one of the neighboring grooves, a flexible sealing surface of the diaphragm being seated within the recess and resiliently biased away from the interface of the valve cap. A plunger assembly is also provided, including plungers movable to push flexible sealing surface towards the communication port.

16 Claims, 11 Drawing Sheets

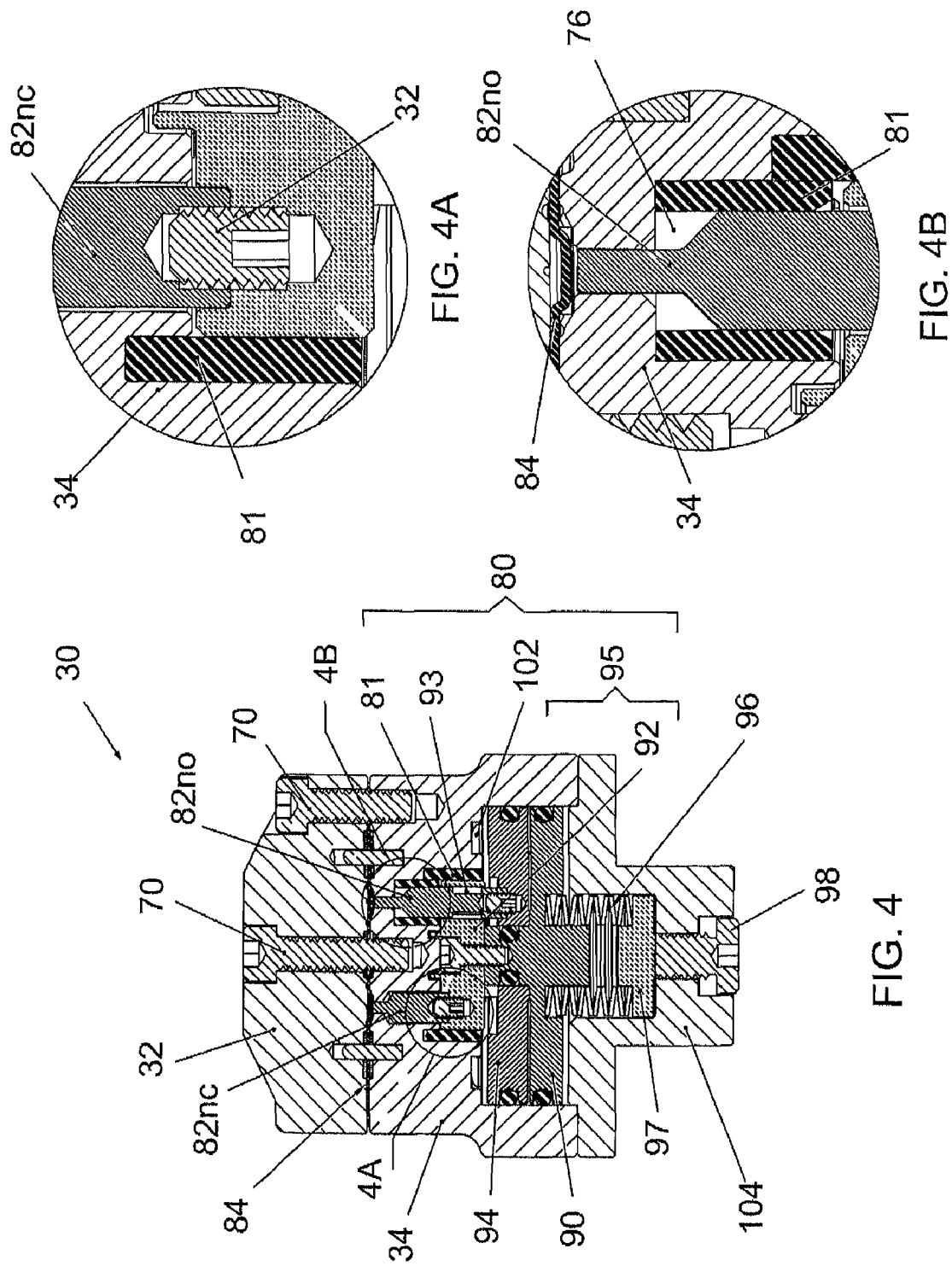

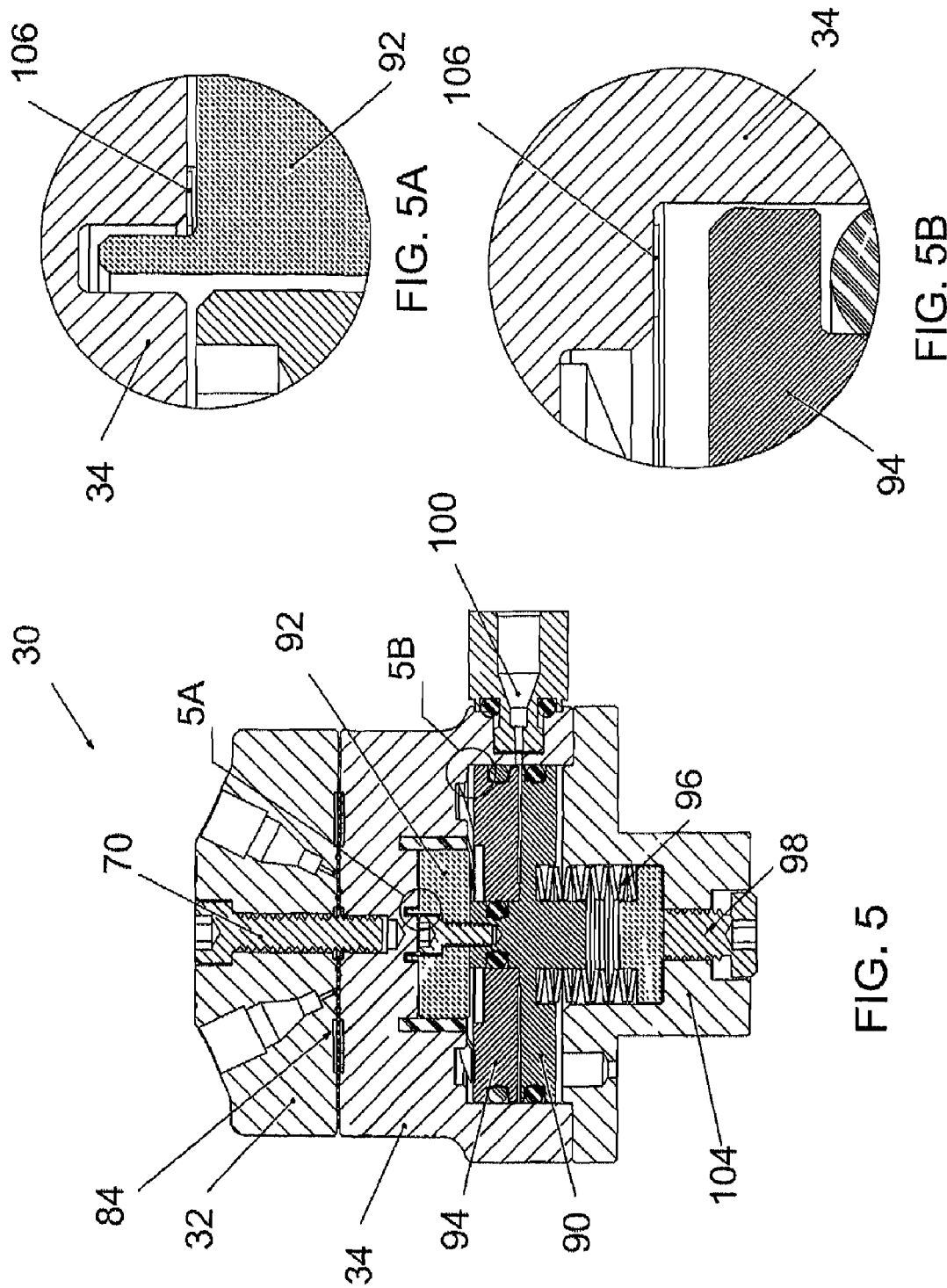

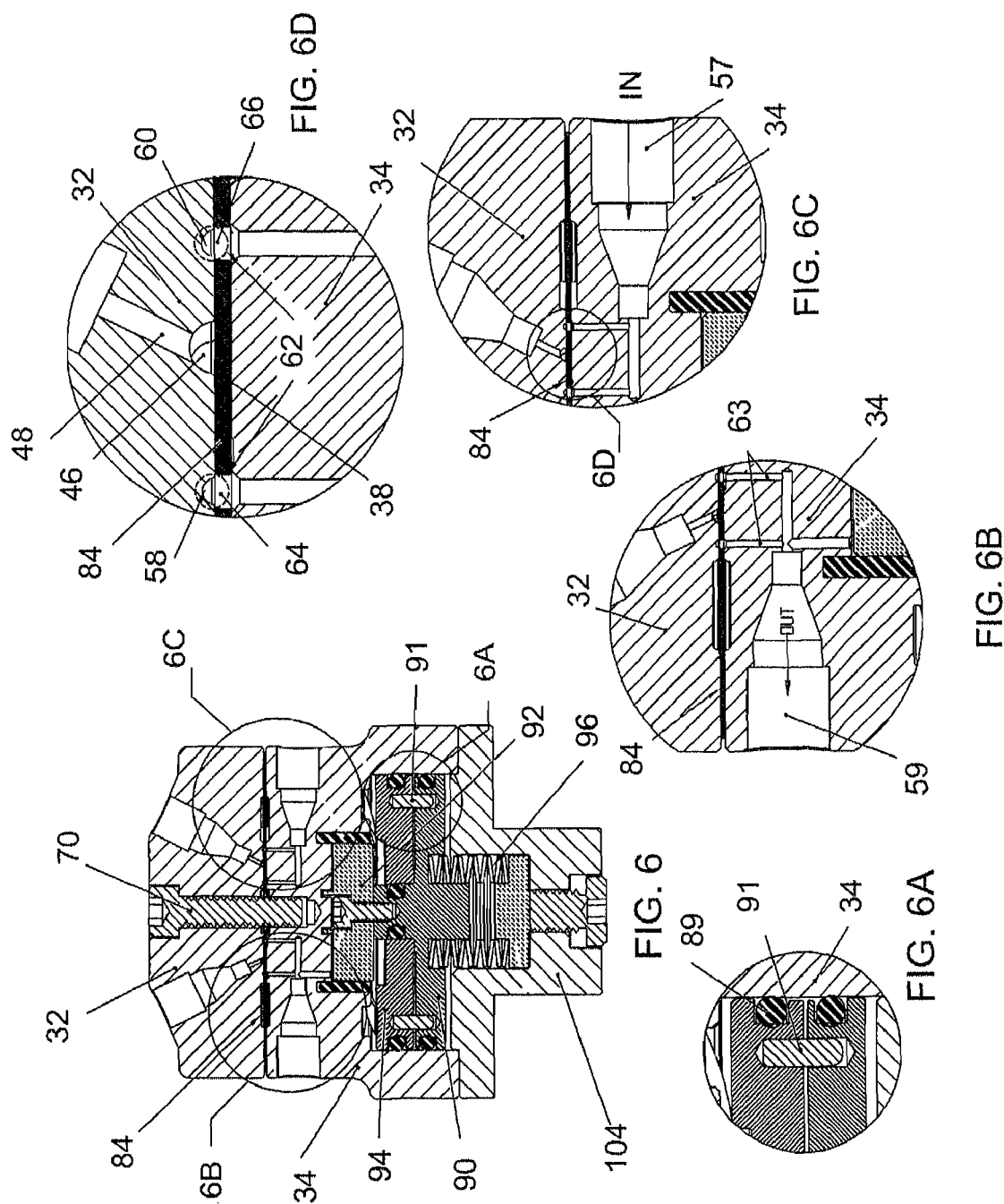

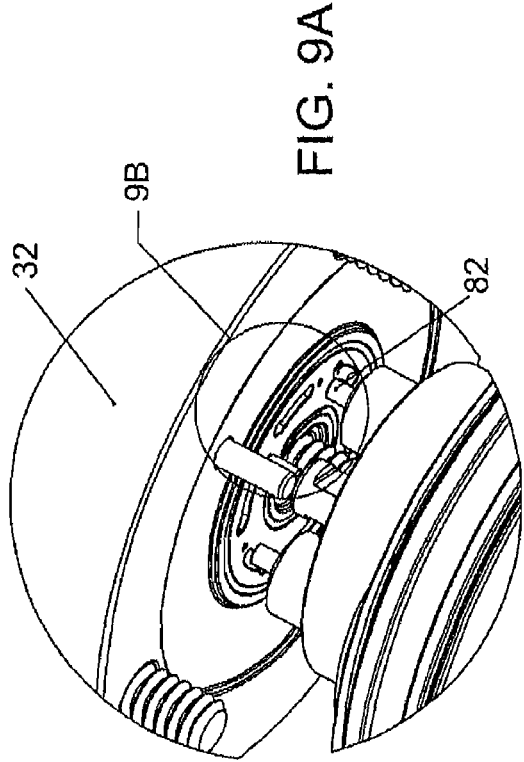
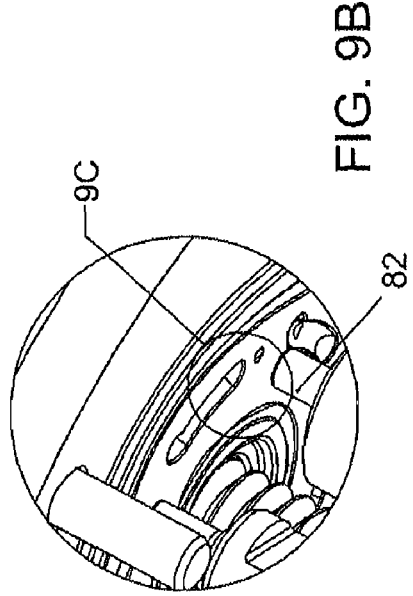
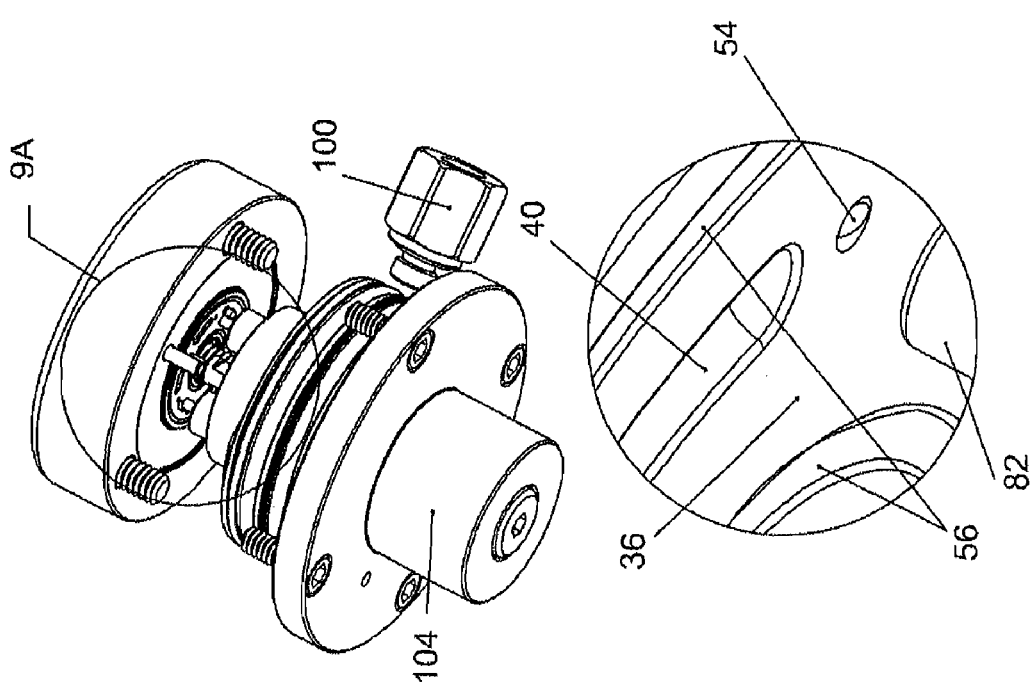
FIG. 9
FIG. 9A
FIG. 9B
FIG. 9C

DIAPHRAGM-SEALED VALVE HAVING INTERMEDIATE COMMUNICATION PORTS

FIELD OF THE INVENTION

The present invention generally relates to fluid analytical systems and more particularly concerns a diaphragm-sealed valve having improved characteristics for use in such systems.

BACKGROUND OF THE INVENTION

As well known by people involved in the art, chromatographic systems rely on the use of valves to allow reproducible sample introduction and various column switching schemes.

For the last forty years, many people have designed diaphragm valves for chromatography. Such diaphragm valves have been used in many commercially available gas chromatographs. They are apt to be integrated more easily in a gas chromatograph due to their physical size and since the actuator is embedded in the valve itself. These characteristics make them attractive for gas chromatograph manufacturers.

Referring to FIG. 1 (PRIOR ART), there is shown an example of a typical diaphragm-sealed valve as known in the art. The valve 1 is provided with a top block 2 having an interface 4 and a plurality of ports 6. Each of the ports 6 opens at the interface 4 and has an inclined thread passage 8 to connect various analytical fitting and tubing (not shown). At the bottom of the inclined thread passage 8, there is a conduit 10 extending in the top block 2 and opening at the interface 4. The ports 6 are arranged on a circular line on the interface 4 of the top block 2. The interface 4 is advantageously flat and polished to minimize leaks between ports and from the ambient atmosphere. The valve 1 is also provided with a bottom block 12 and a diaphragm 14, which is generally made of polyimide, Teflon or other polymer material. The diaphragm 14 is positioned between the top block interface 4 and the bottom block 12, and has a recess therein extending along the circular line formed by the ports 6 and biased away from the interface 4 of the top block 2. The recess 18 in the diaphragm 14 sits in a matching recess 20 made in the bottom block 12, thereby allowing some clearance for fluid circulation between adjacent ports 6.

The valve 1 is also provided with a plurality of plungers 16 mounted in the bottom block 12, each being respectively arranged to be able to compress the diaphragm 14 against the top block 2 at a position located between two of the ports 6. Preferably, as illustrated, when the valve is at rest, three plungers 16 are up while the other three are down. When the plungers are up, they compress the diaphragm 14 against the top block 2 and close the conduits made by the diaphragm recess 18, so that fluid circulation is blocked. The bottom block 12 keeps the plungers 16 and the actuating mechanism in position.

The performance of valves of the type shown in FIG. 1 is generally poor. The leak rate from port to port is too high for most applications and thus limits the system performance. Moreover, the pressure drop on the valve's ports differs from port to port, causing pressure and flow variations in the system. This causes detrimental effects on column performance and detector baseline. Furthermore, many valve designs allow for unacceptable inboard contamination.

As explained above, in the valve of FIG. 1, the sealing of the fluid circulation path between two ports 6 relies simply on the surface of the plunger defining the area that presses the diaphragm recess 18 on the interface 4. This technique imposes tight restrictions on the surface finish and flatness, and on the length of the plungers. Any scratch on the interface 4 or imperfection of the diaphragm 14 will generate leaks. Moreover, the length of all plungers must be the same. Any difference in their lengths will result in leaks, since a shorter plunger will not properly compress the diaphragm against the interface 4.

Several variations of the general concept of the valve of FIG. 1 are known in the art. The main differences relate to the location of the bottom block recess 20. In the past, this recess 20 or its equivalent was located internally in the top block 2, or on its interface 4. U.S. Pat. Nos. 3,111,849; 3,198,018; 3,545,491; 3,633,426 and 4,112,766, which were granted to the same inventors, illustrate valves provided with such recesses. However, as reported in a more recent valve brochure specification entitled "Applied Automation Company, series 11 diaphragm valve" (now commercialized by Siemens), this method is no longer used because of a too high cold flow. Cold flow is also often referred to as cross port flow leak. The latest design from the same group, which was commercialized, uses a flat and polished interface 4 on the top block 2 and a recess 20 in the bottom block 12. In this design, the diaphragm 14 has no recess. Moreover, in order to reduce the cold flow, it was also envisaged to use two diaphragms. U.S. Pat. No. 3,111,849 teaches the use of a "cushion" diaphragm to allegedly compensate for any slight non-parallelism or length difference of plungers. Other attempts have also been made to correct the non-parallelism, as disclosed in U.S. Pat. Nos. 3,376,894; 3,545,491 and 3,633,426, wherein the use of solid plungers has been replaced with the use of small steel balls.

The above-mentioned concern about plunger length has also been taken into consideration in U.S. Pat. No. 6,202,698, granted to Valco Company, which suggests the use of plungers made of softer material. This allows tolerance reduction for the length of such plungers. However, such a design will still result in an important leak rate between ports since the pressure from the plungers is not equal on the diaphragm.

Other attempts have been made in the past to eliminate problems caused by plunger tolerance variations. U.S. Pat. No. 3,139,755 discloses a valve devoid of plungers, hydraulic pressure being used instead. However, an auxiliary source of pressure must be used, since no pneumatic amplification of the pneumatic actuating mechanism is performed. Another design is disclosed in U.S. Pat. No. 3,085,440. In this valve, the diaphragm has been replaced by an O-ring.

In brief, in view of the previously mentioned patents, it can be seen that many attempts have been made to fix cross port leaks problems and outboard or inboard contamination. All of the proposed designs are quite similar with regard to sealing mechanisms, and have the same drawbacks.

There is therefore a need for an improved diaphragm-sealed valve.

SUMMARY OF THE INVENTION

In accordance with a first aspect of the present invention, there is provided a diaphragm-sealed valve that includes a valve cap having a first interface and a plurality of grooves extending in the first interface. The valve cap further includes a plurality of process conduits extending therethrough, each process conduit ending in a process port opening on a corresponding one of the grooves. The valve also includes a valve body having a second interface which faces the first interface of the valve cap. The valve body has a plurality of passages extending transversally therein and a plunger assembly including a plurality of plungers. Each of the plungers is placed in one of the passages and is slideable therein between a closed position, where the plunger projects towards the first interface, and an open position, where the plunger is retracted within the valve body. The valve also includes a diaphragm compressibly positioned between the first and the second interfaces.

The valve also includes at least one communication mechanism each operatively connects a neighbouring pair of grooves. Each communication mechanism includes a communication port opening in the first interface between the grooves of the corresponding pair, a communication conduit extending within the valve cap and connecting the communication port and a first one of the grooves of the pair, a recess within the second interface connected to a corresponding one of the passages and aligned with the communication port and with a second one of the grooves of the pair, and a flexible sealing surface integral to the diaphragm and resiliently biased away from the first interface. The flexible sealing surface is seated within the recess of the second interface when the plunger placed within the corresponding passage is in the open position, the flexible sealing surface sealingly closing the communication port when the plunger is in the closed position.

In accordance with a second aspect of the present invention, there is also provided a valve including a valve cap having a first interface and a plurality of grooves extending in the first interface. The valve cap further includes a plurality of process conduits extending therethrough, each process conduit ending in a process port opening on a corresponding one of the grooves.

The valve also includes a valve body having a second interface facing the first interface of the valve cap. The valve body further has a plurality of passages extending transversally therein, and a plunger assembly. The plunger assembly includes the following components:

- a plurality of plungers each mounted in one of the passages and being slideable therein between a closed position, where the plunger projects towards the first interface, and an opened position, where the plunger is retracted within the valve body. Each plunger is either a normally closed plunger or a normally open plunger;
- a push plate extending within the valve body in parallel to the second interface and movable transversally thereto. The normally closed plungers are mounted on this push plate. A plurality of cavities extend through the push plate for allowing the normally open plungers therethrough;
- an upper piston extending under the push plate contiguously thereto, the normally opened plungers being mounted thereon;
- a lower piston extending under the upper piston contiguously thereto, the lower piston being rigidly connected to the push plate;
- biasing means for upwardly biasing the lower piston and downwardly biasing the upper piston; and
- an actuating mechanism for actuating the plungers between the opened and closed positions thereof. The actuating mechanism controls a distance between the upper and lower pistons.

The valve further includes a diaphragm compressibly positioned between the first and second interfaces, and at least one communication mechanism, each operatively connecting a neighbouring pair of the grooves for allowing fluid communication therebetween.

BRIEF DESCRIPTION OF THE DRAWINGS

These and other objects and advantages of the invention will become apparent upon reading the detailed description and upon referring to the drawings in which:

FIG. 4 is a cross-sectional side view of a diaphragm-sealed valve along line IV-IV of FIG. 3B. FIG. 4A is an enlarged view of section 4A of FIG. 4. FIG. 4B is an enlarged view of section 4B of FIG. 4.

FIG. 5 is a cross-sectional side view of a diaphragm-sealed valve along line V-V of FIG. 3B. FIG. 5A is an enlarged view of section 5A of FIG. 5. FIG. 5B is an enlarged view of section 5B of FIG. 5.

FIG. 6 is a cross-sectional side view of a diaphragm-sealed valve along line VI-VI of FIG. 3B. FIGS. 6A, 6B and 6C are enlarged views of section 6A, 6B and 6C of FIG. 6, respectively. FIG. 6D is an enlarged view of section 6D of FIG. 6C.

FIG. 9 is a partially exploded perspective view of the valve shown in FIG. 2. FIG. 9A is an enlarged view of section 9A of FIG. 9. FIG. 9B is an enlarged view of section 9B of FIG. 9A. FIG. 9C is an enlarged view of section 9C of FIG. 9B.

Figure 1:
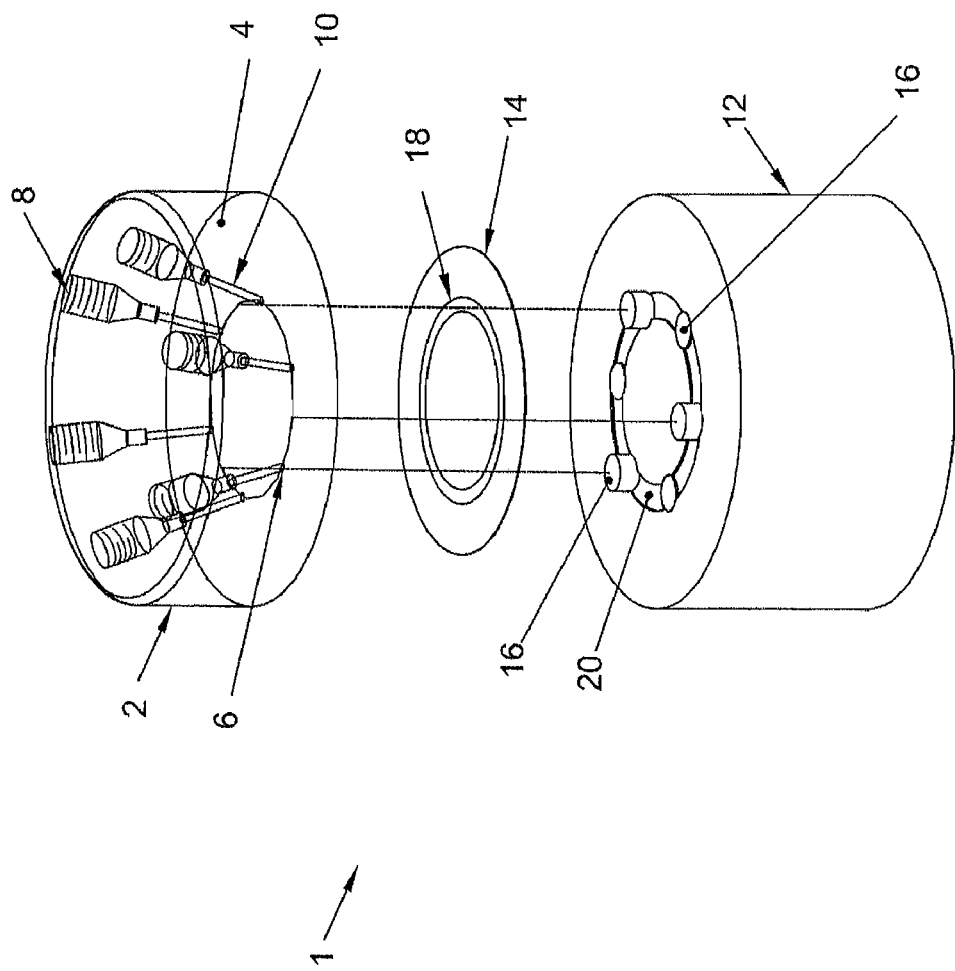
FIG. 1 (PRIOR ART) is an exploded perspective view of a diaphragm-sealed valve known in the art, in partial transparency.

While the invention will be described in conjunction with example embodiments, it will be understood that it is not intended to limit the scope of the invention to such embodiments. On the contrary, it is intended to cover all alternatives, modifications and equivalents as may be included as defined by the present application.

DESCRIPTION OF PREFERRED EMBODIMENTS

In the following description, similar features in the drawings have been given similar reference numerals. To preserve the clarity of the drawings, some references numerals have been omitted, if they were already identified in a preceding figure.

Figure 2:
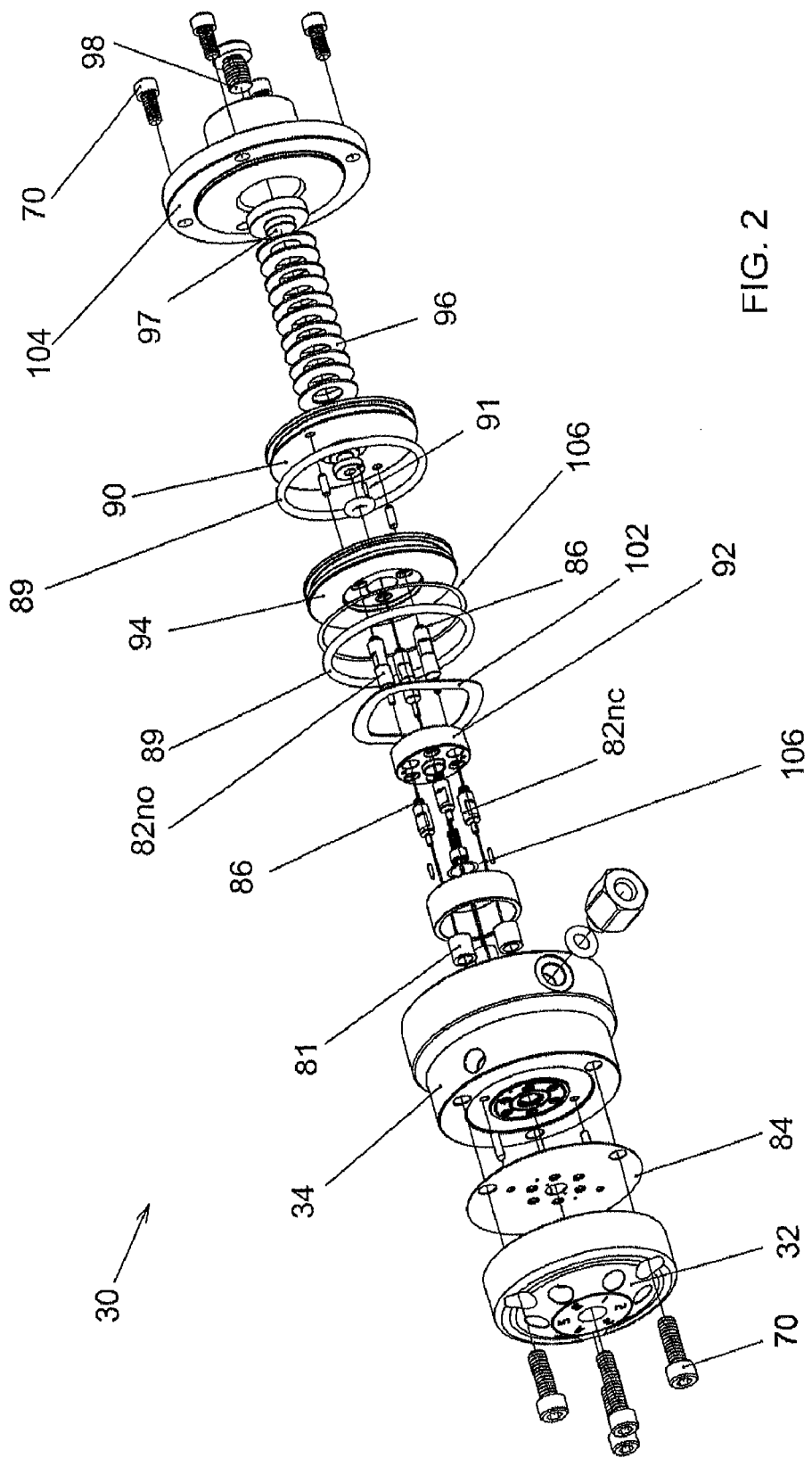
FIG. 2 is an exploded perspective view of a diaphragm-sealed valve according to an embodiment of the invention.
Figure 3A:
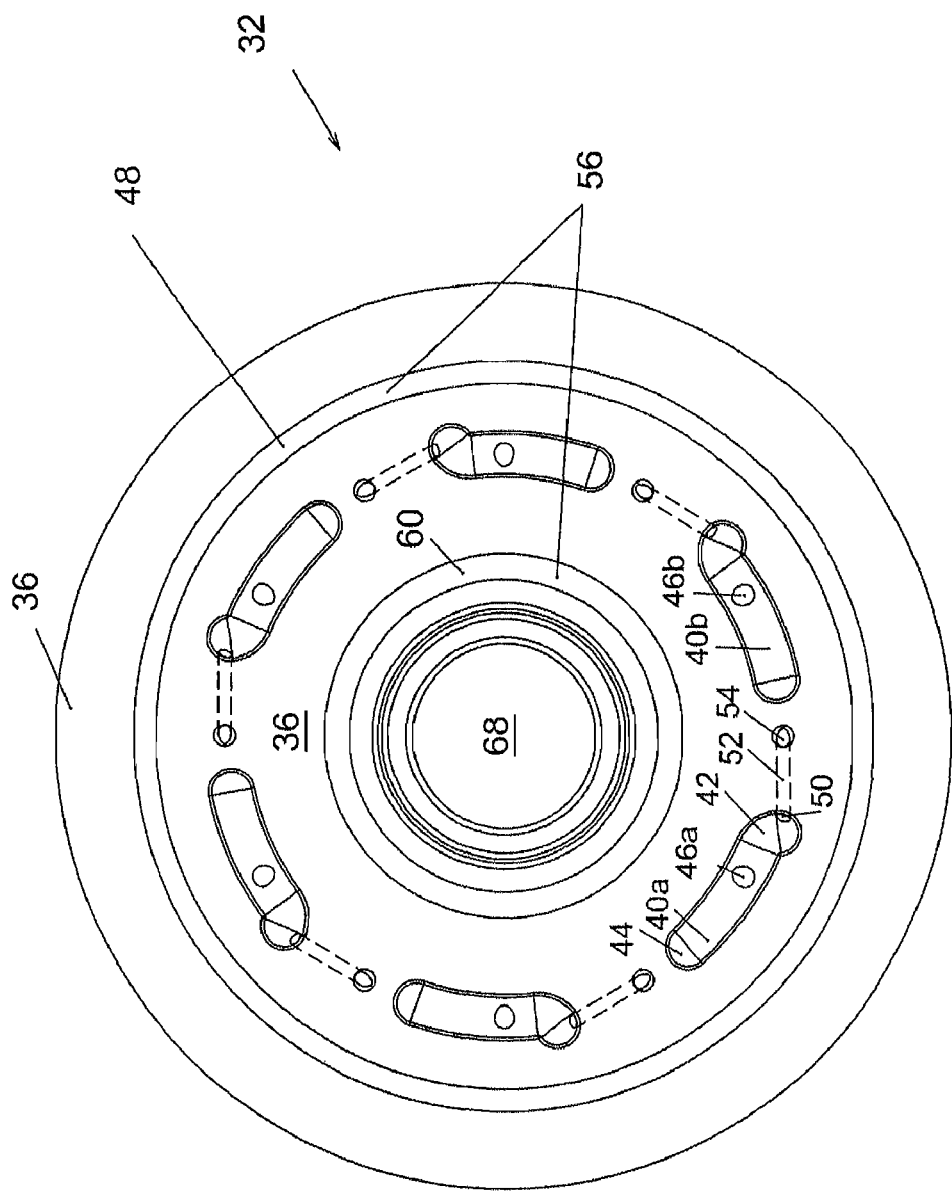
FIG. 3A is a bottom view of the valve cap of a diaphragm-sealed valve according to a preferred embodiment of the present invention.
Figure 3B:
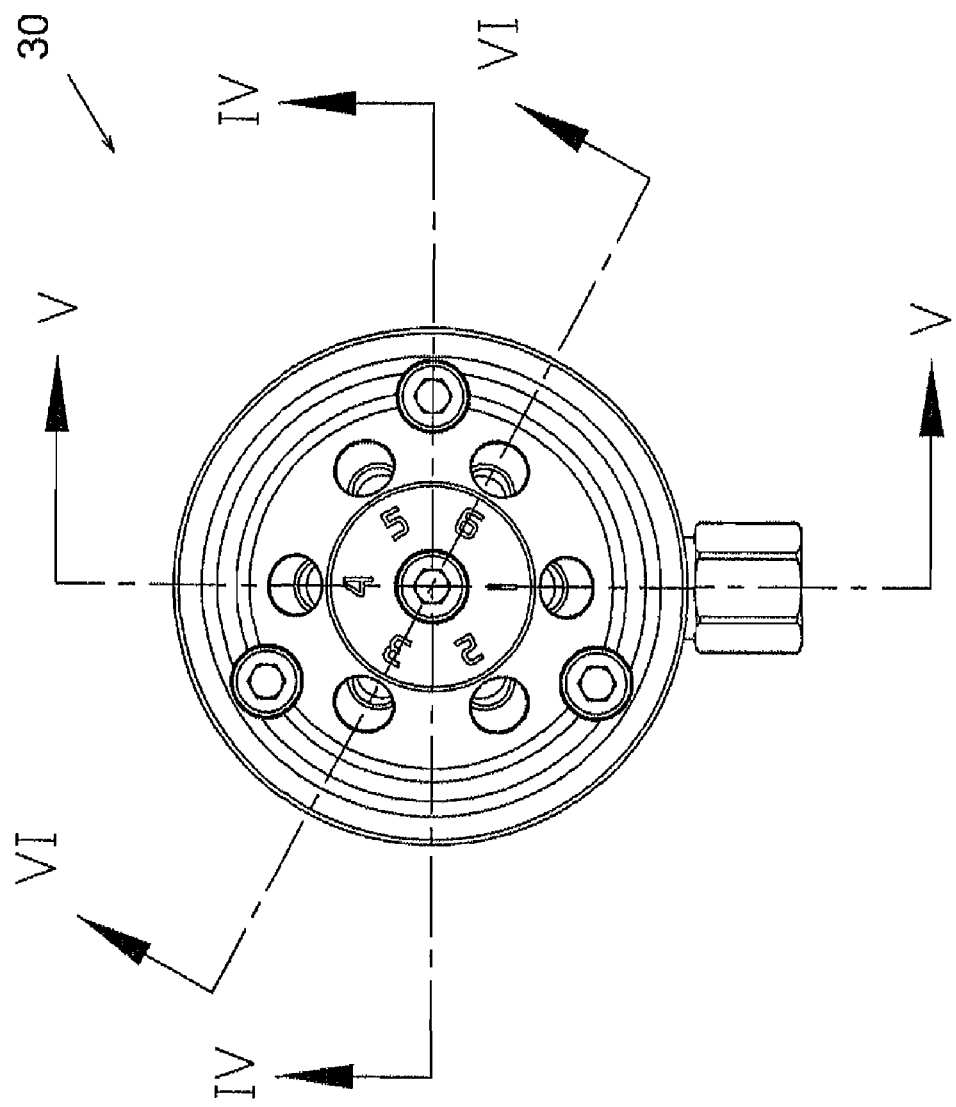
FIG. 3B is a top view of a diaphragm-sealed valve according to a preferred embodiment of the present invention.

Referring to FIGS. 2 and 3B, there is shown a valve 30 according to a preferred embodiment of the present invention.

The valve 30 is of the diaphragm-sealed type, also referred to in the field as a diaphragm based tight shut off valve. Such a valve may be used in analytical equipments of various types, and more particularly chromatographic equipments or online analyzers.

Referring more particularly to FIG. 2, the valve 30 generally includes three main components: a valve cap 32, a valve body 34 and a diaphragm 84 compressibly positioned therebetween. The diaphragm 84 can be made of multiple layers of polymer, with or without a thin metallic layer, or alternatively be made of metal only. Metals that may be used are stainless steel 316, aluminum, chrome-nickel alloy, copper and the like. For applications requiring high gas-tightness sealing, a diaphragm made of multiple layers of polymer is preferably used, while other applications require a thin metallic layer over the polymer layers. Still referring to FIG. 2, at least one communication mechanism is further provided, as will be discussed in detail below.

FIG. 3A shows a bottom view of the valve cap 32, having a smooth surface defining a first interface 36. In this embodiment, the valve cap 32 of the valve 30 is cylindrical and is made of electro-polished stainless steel. A thin layer of polymer may preferably cover the first interface 36 of the valve cap 32. Of course, other materials, for example ceramic or various types of polymers, can be used for the valve cap. Shapes other than a cylindrical one may also be considered.

A plurality of grooves 40, in this particular case six (6), extends in the first interface 36. Throughout the present description, "groove" is understood to mean a channel or a depression formed in the surface defining the first interface 36, of a depth appropriate to allow fluid circulation therein. As shown in FIG. 3A, the grooves 40 are preferably arc-shaped or kidney-shaped, and have first 42 and second 44 ends of rounded form. A corresponding process port 46 opens in each groove 40. Throughout the present description, a "port" refers to an opening for intake or exhaust of a fluid. Preferably, each process port 46 is located closer to the first end 42 of the groove than to the second end 44. In the illustrated embodiment, the grooves are circularly arranged, but they could be placed differently in other embodiments, for example linearly or elliptically. The number of process ports and corresponding grooves may also differ. For example, other embodiments may have 2, 4, 8 or 10 process ports 46.

Referring to FIGS. 6 and 6D, each process port 46 is linked to a process conduit 48 through which sample or carrier fluids are injected or exhausted, as well known in the art. Each process conduit 48 preferably has a narrow cylindrical shape and is connected to valve tubings at one of its ends, while the other end terminates in the corresponding process port 46. The process conduit 48 may alternatively have another shape and may incorporate any appropriate feature known in the art.

Figure 7:
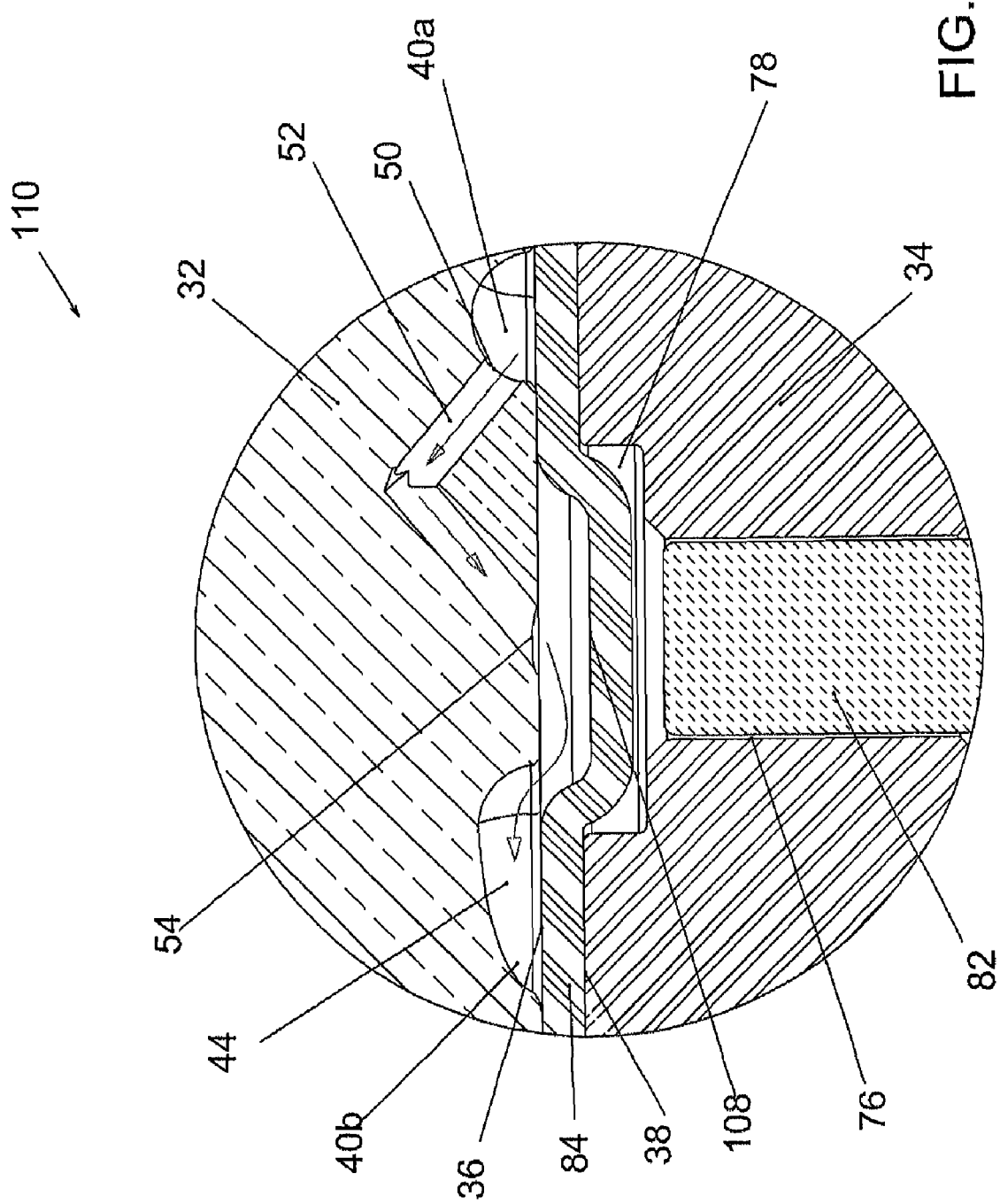
FIG. 7 is a cross-sectional side view of the interface between the plunger and one of the ports of a valve shown according to an embodiment of the invention, with the plunger in a retracted or open position.
Figure 8:
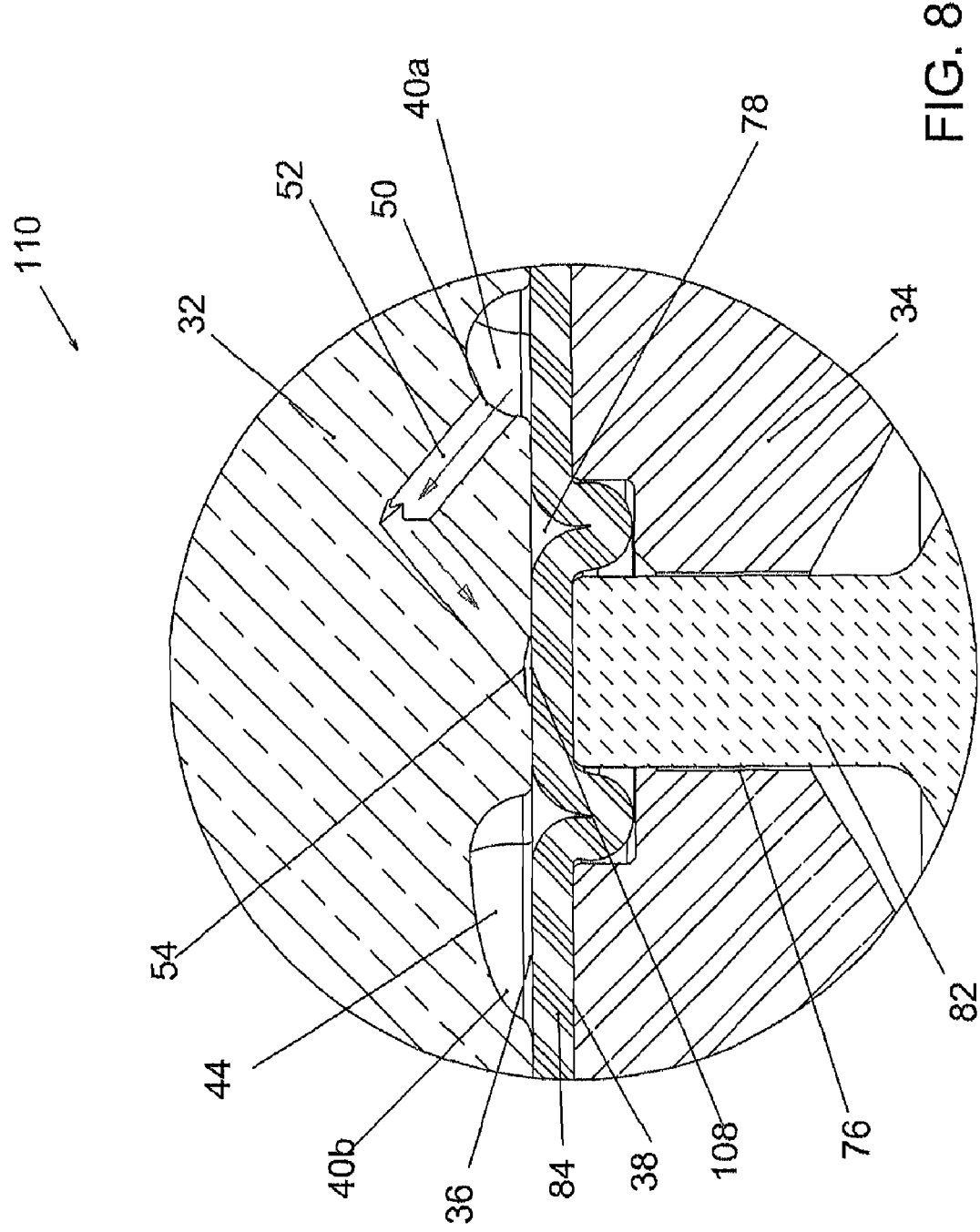
FIG. 8 is a cross-sectional side view of the interface between the plunger and one of the ports of the valve shown in FIG. 7, with the plunger in an upward or closed position.

Referring to FIGS. 7 and 8, the valve body 34 is shown to have a surface defining a second interface 38, which in operation faces the first interface 36 of the valve cap 32. Preferably, the valve body 34 has a cross section of similar dimensions than the valve cap 32. The valve body 34 has a plurality of passages 76 extending transversally therethrough. Proximate the second interface 38, each passage 76 has the shape of a cylinder having one extremity opening at the second interface 38 in a recess 78, the diameter of the recess 78 being larger than the diameter of the corresponding passage 76. The valve body 34 also includes a plunger assembly including a plurality of plungers 82, each mounted in a corresponding passage 76. Each plunger 82 is slideable between a closed and an open position. FIG. 7 shows a plunger 82 retracted within the valve body 34, defining the open position according to an embodiment of the invention. FIG. 8 shows the plunger 82 of the same embodiment in the closed position where it projects towards the first interface 36.

Referring to FIG. 4, a portion of a plunger assembly 80 is illustrated according to an embodiment of the invention. More particularly, FIG. 4 shows two (2) of the (6) plungers 82 of the embodiment of FIG. 2. The term "plunger" is understood to mean a mechanism component driven by or against a mechanical force or fluid pressure. As mentioned above, each plunger 82 is slideable in a corresponding passage 76 of the valve body 34. The diameter of a passage 76 is slightly larger than that of its corresponding plunger 82. Preferably, a guide sleeve 81 surrounds the passage, for facilitating the movement of the plunger into the passage. The left side plunger of FIG. 4 is shown in the closed position, whereas the right side plunger is shown in the open position.

Preferably, when in the closed position, the contact area of each plunger 82 is pushed evenly throughout its surface. Thus, all mechanic or fluid forces are transferred equally onto the diaphragm 84 This design ensures that the plungers 82 remain substantially vertical when actuated.

According to embodiments of the invention, the plungers are preferably of two types, designated as "normally closed" (nc) and "normally open" (no). In typical chromatography applications, the plungers of a given type are actuated together, so that they are either all in the closed position or all in the open position. As their names indicate, the nc plungers are biased towards the closed position, whereas the no plungers are biased towards the open position.

The plungers 82 may be actuated by an actuating mechanism. An example of an actuating mechanism is shown with reference to FIGS. 4, 4A, 4B and 5. In the illustrated embodiment, it can be seen that the normally closed plungers 82nc have a length different than the length of the normally open plunger 82no. A push plate 92 extends within the valve body 34 in parallel to the second interface 36, and is movable transversally thereto. The normally closed plungers 82nc are mounted on this push plate 92. An upper piston 94 extends contiguously under the push plate 92. The normally open plungers 82no are mounted on the upper piston 94. A plurality of cavities 93 extend across the push plate 92 for allowing the normally open plungers therethrough. In the illustrated embodiment, the plungers 82 are affixed to either the push plate 92 or the upper piston 94 through a fixed fastener such as screws 86, which advantageously allows the valve to be fully operational regardless of its orientation. It will therefore be understood by one skilled in the part that the reference to the directions "up" and "down" throughout the present application is used for ease of reference to the drawings, particularly FIGS. 4 through 6D, and is not meant to indicate a preferred orientation of the valve in use.

A lower piston 90 extends contiguously under the upper piston 94 and is rigidly connected to the push plate. The lower piston 90 and push plate 92 therefore move together within the valve body 34. Dowel pins 91 may be provided to prevent the upper 94 and lower 90 pistons from rotating with respect to each other, and O-rings 89 are preferably provided to properly seal the upper 94 and lower 90 pistons. (see FIGS. 6 and 6A).

The lower piston 90, push plate 92 and the normally closed plungers 82nc thereon are biased upward by appropriate means. In the illustrated embodiment, a Belleville assembly 95, including a Belleville washer stack 96 and a plate 97, cooperates with the lower piston 90. The upward force on the Belleville assembly 95 is controlled by a compression set screw 98. The lower piston 90 therefore pushes the plunger push plate 92 and keeps the normally closed plunger 82nc in the closed position when no opposite force is applied thereon. A bottom cap 104 closes the valve at its bottom end. Of course, the Belleville washer 96 may be replaced by any other biasing means, such as standard springs or polymer bushings.

The upper piston 94 is for its part biased downward by appropriate means. In the illustrated embodiment, disc spring 102 extends from within the valve body 34 over the upper piston 94, and applies a downward force thereon when no opposite force is in play. The normally open plungers 82no mounted on the upper piston 94 are therefore biased towards the open position.

An actuating mechanism is provided for actuating the plungers 82 of both types between their open and closed positions thereof. This can be accomplished in the current embodiment by controlling the distance between the upper and lower pistons 94 and 90. When not actuated, the two pistons are in contact, as they are pushed towards each other by the Belleville assembly 95 and disc spring 102. Referring to FIG. 5, the actuating mechanism preferably includes a pneumatic actuator formed by the two pistons 90,94, the push plate 92 and the Belville washer 96, and further includes a solenoid valve (not shown) or other appropriate system for supplying pressurised gas between the upper and lower pistons 94 and 90 through a cylinder port 100. The gas will counterbalance the bias of both pistons by pushing the upper piston 94 upward, thus sliding the normally open pistons 82no towards the closed position, and by pushing the lower piston 90 downwards, thus pulling the push plate 92 downward and retracting the normally closed pistons 82nc towards the open position. Removing the pressurized gas will have the opposite result, due to the biasing effect of the Belleville assembly 95 and disc spring 102.

Referring to FIGS. 5A and 5B, according to one embodiment of the invention, shims 106 are used within the valve body to limit the stroke of the lower and upper pistons 90, 94. Using shims of the proper thickness allows the use of a higher actuating pressure without requiring the use a pressure regulator to drive the valve, as in valves of the prior art.

Referring to FIGS. 2, 4, 5, and 6, according to one embodiment of the invention the valve cap 32 and valve body 34 are held together by an appropriate number of holding screw 70. In the illustrated embodiment, four (4) holding screws are provided, one in the center of the valve and the other forming a triangle there around. Of course, the holding screws could be provided in a different number and at different location, or other types of fasteners could be used so that the valve cap and valve body are held tightly together.

The valve 30 may optionally be provided with a purge circulation line 56 for preventing inboard and outboard leaks. Referring to FIG. 3, the purge circulation line 56 may include an outer annular channel 58 extending outwardly of the grooves 40 in the first interface 36, and an inner annular channel 60 also extending in the first interface 36 but inwardly of the grooves 40. Referring to FIGS. 6, 6B, 6C and 6D, the purging line preferably includes a pair of fluid inlet 62 and fluid outlets 63. Each pair has a first opening 64 in the inner annular channel 60 and a second opening 66 in the outer annular channel 58, for providing a continuous fluid flow in each channel. Purging fluid is provided to the fluid inlets 62 through inlet cylinder port 57 and extracted through outlet cylinder port 59. The outlet cylinder port 59 of the purge circulation line may also be connected to monitoring means 112, so that a fluid leak captured by the purge line be detected.

As mentioned above, in accordance with a preferred embodiment of the invention there are provided communication mechanisms each operatively connecting a neighbouring pair of the grooves in the valve cap. On such mechanism is provided between each pair of ports between which fluid communication need to be alternatively allowed and interrupted. Such a communication mechanism will now be described with reference to FIGS. 3, 7, 8 and 9.

The communication mechanism first includes a communication port 54 opening in the first interface 36 at an intermediate position between the grooves to be operatively connected. The communication port is itself connected to a communication conduit 52 which extends within the valve cap 32. The communication conduit 52 a port 50 opposite the communication port 54 opening in a first one 40a of the grooves of a pair. Each of the communication conduits 52 of this preferred embodiment is drilled into the valve cap 32, and has a shape of an inverted V with a circular cross section, the diameter of the communication port 54 being slightly larger than the diameter of the communication conduit 52. Of course, the internal communication conduit may have other appropriate shape.

As mentioned above, the valve body is provided with recesses 78 within the second interface 38 and connected to corresponding passages 76. The communication mechanism includes one such recess 78, which is aligned with both the corresponding communication port 54 and with the second one 40b of the grooves of the pair.

The diaphragm 84 is provided with a plurality of flexible sealing surface 108 each integral thereto and each part of a corresponding communication mechanism. For a given communication mechanism, therefore, the flexible sealing surface 108 is resiliently biased away from the first interface 36, and is seated within the recess 78 when the plunger 82 mounted within the corresponding passage 76 is in the open position. This position is shown in FIG. 7. When the plunger is in the closed position, as seen in FIG. 8, it pushes up on the sealing surface 108 of the diaphragm 84, which sealingly closes the communication port 54.

In another preferred embodiment, the flexible sealing surfaces 108 may also be attached to the plungers, so that when the valve 30 is used in sub-atmospheric pressure applications, the sealing surfaces 108 are pulled towards the bottom of the recesses 78 when their corresponding plungers are retracted towards the open position.

In use, when the plunger 82 is in the opened position (as shown in FIG. 7), fluid communication is allowed between neighbouring process ports 46a and 46b. Fluid exits the process port 46a within the corresponding groove 40a, which is surrounded by the diaphragm 84. Fluid can therefore only exit through port 50 of the communication conduit 52, which carries it the communication port 54. As the flexible sealing surface is biased towards the bottom of the recess 78, fluid is allowed within this recess 78 which allows it to flow to the neighbouring groove 40b, where is exits the valve through the corresponding process port 46b. When the plunger 82 is in the closed position (as shown in FIG. 8), the flexible sealing surface 108 of the diaphragm is pushed towards the communication port 54, which is therefore completely blocked thereby preventing fluid from exiting the communication conduit 52. Communication between the two process ports 46a and 46b is therefore prevented. Preferably the diameter of the communication port 54 is smaller than the diameter of the plunger 82, effectively ensuring gas or liquid tightness.

As will be readily understood by one skilled in the art, the communication mechanism as explained above allows a positive shut-off on a communication port, the shut-off interrupting a flow between two adjacent process ports. Traditional gas chromatography diaphragm valves of the prior art interrupt the flow between two adjacent process ports by forcing a diaphragm on a surface between two process ports, rather than on an intermediate port.

Figure 10A:
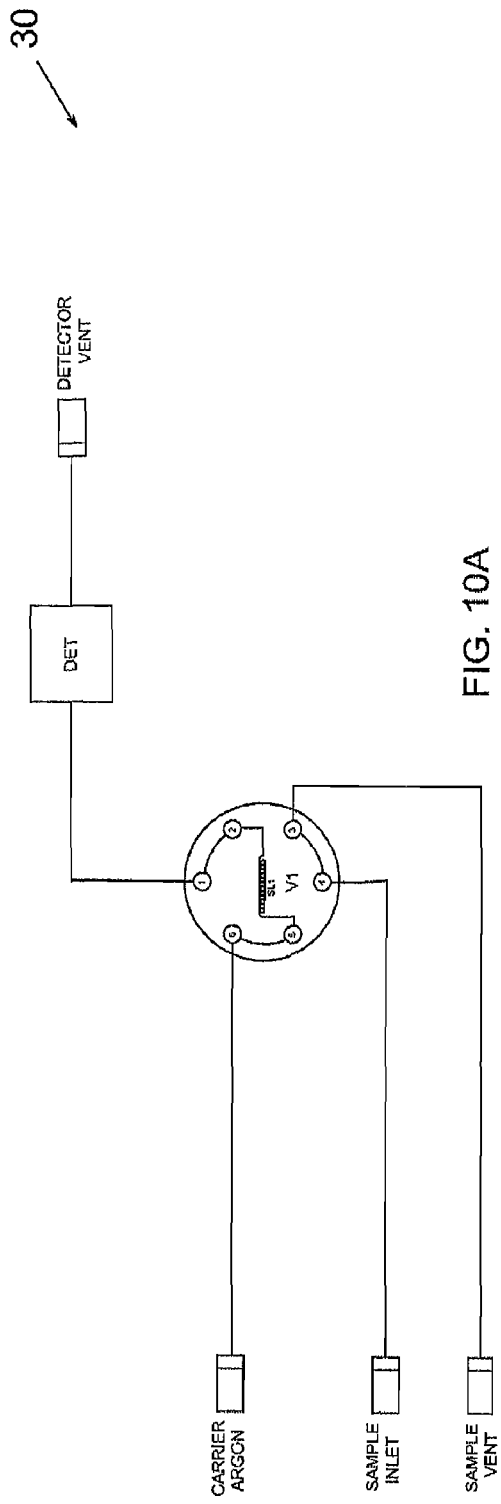
FIG. 10A is a schematic representation of a typical chromatographic application using a valve according to an embodiment of the present invention, the valve being in an "on" position.
Figure 10B:
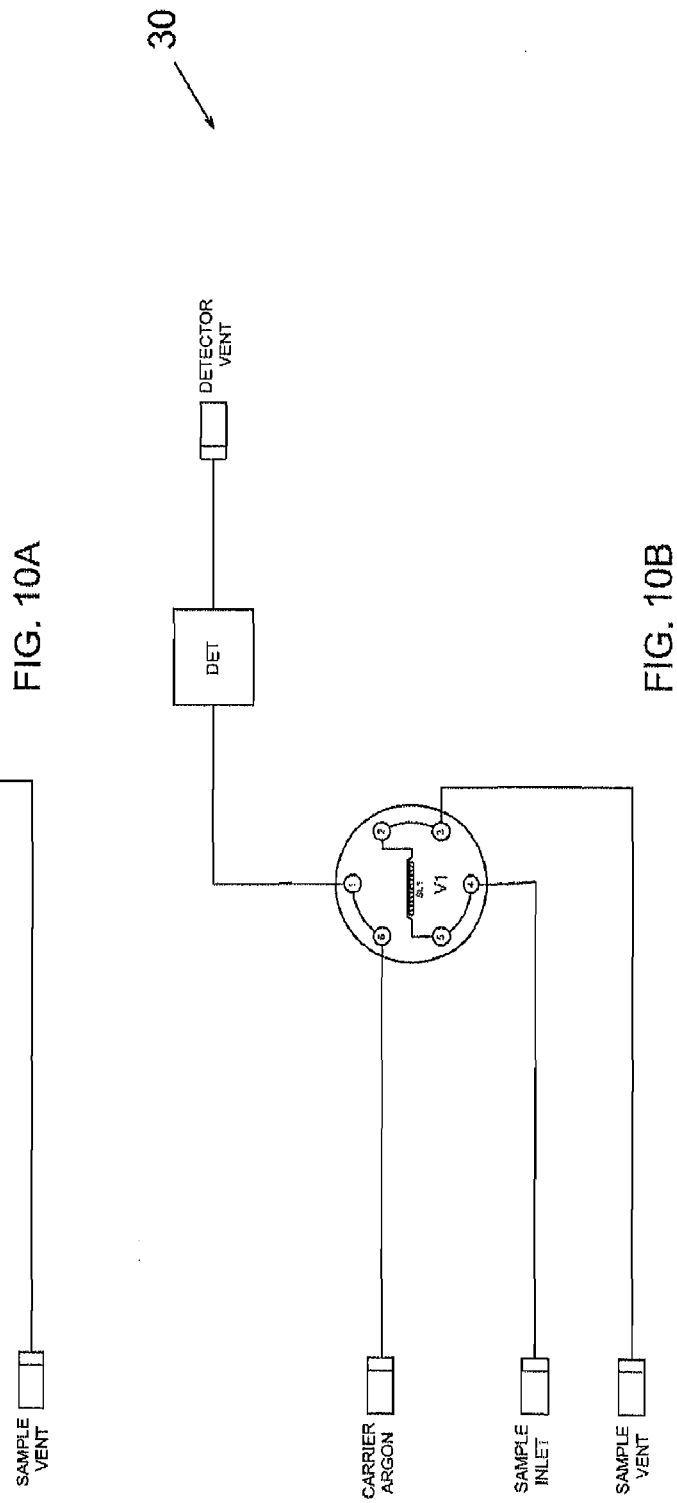
FIG. 10B is a schematic representation of the chromatographic application illustrated in FIG. 10A, the valve being in an "off" position.

In a preferred embodiment of the invention, as shown in the schematic representation of FIGS. 10A and 10B, a diaphragm-sealed valve 30 allows for a traditional flow path found in chromatographic instruments. With this valve type, there is usually a continuous flow of fluid or liquid through all ports at all times, unless the valve is actuated. When the valve is actuated, all ports are closed to avoid an undesired mix of fluid or liquid within the valve. FIG. 10A shows the valve in an "on" configuration, where the sample is injected into the carrier circuit, and FIG. 10B shows the valve in an "off"

configuration, where the sample loop is filled and swept with the sample gas. While the preferred embodiment concerns a valve used for a sample loop injection configuration, other configurations such as hearcut, back flush, column selection can be realized.

Although preferred embodiments of the present invention have been described in detail herein and illustrated in the accompanying drawings, it is to be understood that the invention is not limited to these precise embodiments and that various changes and modifications may be effected therein without departing from the scope or spirit of the present invention.

The invention claimed is:

1. A valve comprising:
   a valve cap having a first interface and a plurality of grooves extending in said first interface, the valve cap further comprising a plurality of process conduits extending therethrough, each process conduit ending in a process port opening on a corresponding one of the grooves;
   a valve body having a second interface facing the first interface of the valve cap, the valve body comprising a plurality of passages extending transversally therein and a plunger assembly comprising a plurality of plungers each placed in one of said passages and being slideable therein between a closed position where said plunger projects towards the first interface and an open position where said plunger is retracted within said valve body;
   a diaphragm compressibly positioned between the first and second interfaces; and
   at least one communication mechanism each operatively connecting a neighbouring pair of said grooves, each communication mechanism comprising:
      a communication port opening in the first interface between the grooves of the corresponding pair;
      a communication conduit extending within the valve cap and connecting the communication port and a first one of the grooves of said pair;
      a recess within the second interface connected to a corresponding one of the passages and aligned with the communication port and with a second one of the grooves of said pair; and
      a flexible sealing surface integral to the diaphragm and resiliently biased away from the first interface, the flexible sealing surface being seated within the recess of the second interface when the plunger placed within the corresponding passage is in the open position, said flexible sealing surface sealingly closing the communication port when said plunger is in the closed position.

2. A valve according to claim 1, wherein the plurality of grooves are circularly arranged on the first interface.

3. A valve according to claim 1, wherein each groove of the plurality of grooves is arc-shaped.

4. A valve according to claim 1, wherein each plunger of the plunger assembly is either a normally closed plunger or a normally open plunger.

5. A valve according to claim 4, wherein the plunger assembly comprises:
   a push plate extending within the valve body in parallel to the second interface and movable transversally thereto, the normally closed plungers being mounted on said push plate, a plurality of cavities extending across said push plate for allowing the normally open plungers therethrough;
   an upper piston extending under the push plate contiguously thereto, the normally opened plungers being placed thereon;
   a lower piston extending under the upper piston contiguously thereto, the lower piston being rigidly connected to the push plate;
   biasing means for upwardly biasing the lower piston and downwardly biasing the upper piston; and
   an actuating mechanism for actuating the plungers between the opened and closed positions thereof, the actuating mechanism controlling a distance between the upper and lower pistons.

6. A valve according to claim 5, wherein the biasing means comprise a Belleville washer assembly cooperating with the lower piston and a screw for controlling an upward force on said Belleville washer assembly.

7. A valve according to claim 5, wherein the biasing means comprise a disc spring extending over the upper piston.

8. A valve according to claim 1, further comprising a layer of a polymer covering the first interface of the valve cap.

9. A valve according to claim 1, wherein the flexible sealing surface of each communication mechanism is attached to the plunger placed within the corresponding passage.

10. A valve according to claim 1, wherein the diaphragm comprises multiple layers made of a polymer, multiple layers of polymer covered with a layer of metal or multiple layers of metal.

11. A valve according to claim 1, wherein for each communication mechanism, the recess and the corresponding passage have a cylindrical shape, the recess having a diameter larger than a diameter of the corresponding passage.

12. A valve according to claim 1, wherein the communication port of each of said communication mechanism has a surface smaller than a surface of an end of the plunger mounted within the corresponding passage aligned with said communication port.

13. A valve according to claim 1, wherein the communication port of each of said communication mechanism is closer to the second one of the grooves of the pair then to the first one of the grooves of said pair.

14. A valve according to claim 1, wherein the communication conduit of each of the communication mechanism is shaped as an inverted V.

15. A valve according to claim 1, further comprising a purge circulation line comprising:
   an outer annular channel extending in the first interface outwardly of said grooves;
   an inner annular channel extending in the first interface inwardly of said grooves;
   a pair of fluid inlet and fluid outlets, each pair having a first opening in the first annular channel and a second opening in the second annular channel, for providing a continuous fluid flow in the first groove and in the second groove.

16. A valve according to claim 1, wherein the valve cap and valve body are cylindrical and comprise six of said grooves and six corresponding communication mechanisms, wherein the grooves are arc-shaped and are circularly arranged on the first interface and wherein two adjacent plunger assemblies comprise a normally closed plunger and a normally open plunger.

* * * * *